(12) United States Patent
Dayton et al.

(10) Patent No.: US 11,324,930 B2
(45) Date of Patent: May 10, 2022

(54) MEDICAL GUIDEWIRES WITH CONTROLLABLE FEATURES

(71) Applicant: Boston Scientific Scimed, Inc., Maple Grove, MN (US)

(72) Inventors: Peter Dayton, Brookline, MA (US); Kevin James McElwee, Berwick, ME (US); Paul Smith, Smithfield, RI (US); Dane Seddon, Boston, MA (US); James Scutti, Arlington, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 457 days.

(21) Appl. No.: 16/270,094

(22) Filed: Feb. 7, 2019

(65) Prior Publication Data

US 2019/0240461 A1 Aug. 8, 2019

Related U.S. Application Data

(60) Provisional application No. 62/628,124, filed on Feb. 8, 2018.

(51) Int. Cl.
*A61M 25/09* (2006.01)
*A61M 25/01* (2006.01)
*A61M 25/06* (2006.01)

(52) U.S. Cl.
CPC ........ *A61M 25/09* (2013.01); *A61M 25/0127* (2013.01); *A61M 25/0136* (2013.01); *A61M 25/0155* (2013.01); *A61M 25/0662* (2013.01); *A61M 2025/091* (2013.01); *A61M 2025/09125* (2013.01); *A61M 2025/09133* (2013.01); *A61M 2025/09175* (2013.01)

(58) Field of Classification Search
CPC .............. A61M 25/04; A61M 25/0041; A61M 25/0662; A61M 25/09; A61M 25/0127; A61M 25/0136; A61M 25/0155; A61M 2025/091; A61M 2025/09125; A61M 2025/09133; A61M 2025/09175; A61M 25/00; A61M 35/0158; A61M 2025/0058; A61M 2025/0293; A61M 2205/0272–0294; A61B 2017/22047; A61B 2017/2204
USPC ........................................................ 600/585
See application file for complete search history.

(56) References Cited

U.S. PATENT DOCUMENTS

| | | | |
|---|---|---|---|
| 4,676,249 A | 6/1987 | Arenas et al. | |
| 5,040,543 A | 8/1991 | Badera et al. | |
| 5,313,967 A | 5/1994 | Lieber et al. | |
| 5,542,938 A | 8/1996 | Avellanet et al. | |
| 5,706,827 A | 1/1998 | Ehr et al. | |
| 5,797,856 A | 8/1998 | Frisbie et al. | |

(Continued)

*Primary Examiner* — Christian Jang
*Assistant Examiner* — Anna Roberts
(74) *Attorney, Agent, or Firm* — Bookoff McAndrews, PLLC

(57) ABSTRACT

According to one aspect, a guidewire assembly for positioning within a body of a patient may include a guidewire shaft having a proximal section and a distal section. The distal section may be configured to move within the body of a patient when the guidewire assembly is in a first operating state. The distal section may be configured to expand radially outward when the guidewire assembly is in a second operating state to engage an interior surface of the body and inhibit movement of the guidewire shaft.

20 Claims, 4 Drawing Sheets

(56) References Cited

U.S. PATENT DOCUMENTS

| | | | |
|---|---|---|---|
| 10,016,206 B1* | 7/2018 | Yang | A61B 17/221 |
| 2007/0021685 A1* | 1/2007 | Oepen | A61M 25/09 |
| | | | 600/585 |
| 2007/0135713 A1 | 6/2007 | Borgert et al. | |
| 2014/0180166 A1 | 6/2014 | Isch | |
| 2014/0257138 A1 | 9/2014 | Hui et al. | |
| 2015/0306350 A1* | 10/2015 | Hofius | A61M 25/005 |
| | | | 604/506 |
| 2016/0101267 A1 | 4/2016 | Kelly | |
| 2017/0143938 A1* | 5/2017 | Ogle | A61M 25/0074 |

* cited by examiner

MEDICAL GUIDEWIRES WITH CONTROLLABLE FEATURES

CROSS-REFERENCE TO RELATED APPLICATIONS

This application claims the benefit of priority from U.S. Provisional Application No. 62/628,124, filed on Feb. 8, 2018, which is incorporated by reference herein in its entirety.

TECHNICAL FIELD

Various aspects of the present disclosure relate generally to medical systems, devices, and related methods. More specifically, the present disclosure relates to medical systems, devices, and methods for positioning one or more medical devices within a body lumen.

BACKGROUND

Medical procedures that involve navigating to a site within the body often require a medical guidewire. Guidewires are used in numerous catheterization procedures and other medical procedures as an aid to placement of a catheter or other device at a selected site within the human body. Guidewires may be advanced under direct visualization through an endoscope with or without fluoroscopy. Typically, guidewires are lubricious to facilitate easy tracking in small tubular body lumens. The low friction from the lubrication facilitates force transmission and fine movement when small forces are exerted on the proximal end of the wire. Once placed proximate to target anatomy, maintenance of the guidewire position is desirable for the safety and efficiency of a procedure. However, lubrication on the guidewire often results in movement away from target anatomy. In some examples, a user may locate target anatomy within a body lumen and begin a procedure at the target anatomy, followed by the guidewire shifting its position during the procedure. When the guidewire shifts its position, the user may lose track of the target anatomy requiring repositioning of the guidewire before resuming the procedure. Guidewire movement after the target anatomy has been reached may prolong a procedure and/or increase the likelihood of a complication or a failed procedure.

The systems, devices, and methods of the current disclosure may rectify some of the deficiencies described above, and/or address other aspects of the prior art.

SUMMARY

Examples of the present disclosure relate to, among other things, medical systems, devices, and methods. Each of the examples disclosed herein may include one or more of the features described in connection with any of the other disclosed examples.

According to one aspect, a guidewire assembly for positioning within a body of a patient may include a guidewire shaft having a proximal section and a distal section. The distal section may be configured to move within the body of a patient when in a first operating state of the guidewire assembly. The distal section may be configured to engage an interior surface of the body when in a second operating state of the guidewire assembly, to inhibit movement of the guidewire shaft. The guidewire assembly may also include a lumen within the guidewire shaft and extending from the proximal section to the distal section. Also, the guidewire assembly may include at least one opening in a wall of the distal section and in fluid communication with the lumen. The guidewire assembly may further include a vacuum source in fluid communication with the lumen and configured to provide suction to the at least one opening. The vacuum source may not apply a suction force to the lumen when the guidewire assembly is in the first operating state.

In other aspects of the present disclosure, the guidewire assembly may include one or more of the features below. A vacuum force may be applied to the lumen when the guidewire assembly is in the second operating state. The at least one opening may include multiple openings positioned around a circumference of the guidewire shaft. In some examples, the multiple openings may include at least ten openings positioned about only a portion of the circumference of the guidewire shaft.

In other aspects, a guidewire assembly for positioning within a body of a patient may include a guidewire shaft having a proximal section and a distal section. The distal section may be configured to move within the body of a patient when in a first operating state of the guidewire assembly. The guidewire assembly may also include a lumen within the guidewire shaft extending from the proximal section to the distal section. Also, the guidewire assembly may include an opening in a wall of the distal section and in communication with the lumen. The guidewire assembly may further include a wire longitudinally movable within the lumen. A distal portion of the wire may have a preset, non-straight configuration when under no constraining force. The distal portion of the wire may be configured to assume the preset configuration when extended outward from the opening to engage the body of the patient and inhibit movement of the guidewire assembly in a second operating state of the guidewire assembly.

In other aspects of the present disclosure, the guidewire assembly may include one or more of the features below. The wire may comprise a metal from the nitinol, stainless steel or cobalt-chromium families of alloys. The preset non-straight configuration may include one of a spiral shape, a helical shape, or a curved shape.

In other aspects, a guidewire assembly for positioning within a body of a patient may include a guidewire shaft having a proximal section and a distal section. The distal section may be configured to move within the body of a patient when the guidewire assembly is in a first operating state. Also, the distal section may be configured to expand radially outward when the guidewire assembly is in a second operating state to engage an interior surface of the body and inhibit movement of the guidewire shaft.

In other aspects of the present disclosure, the guidewire assembly may include one or more of the features below. The guidewire assembly may further include at least one movable member coupled to the distal section of the guidewire shaft. The moveable member may include a magnetic material and may move radially outward when the guidewire assembly transitions from the first operating state to the second operating state. The guidewire assembly may also include an electromagnetic coil positioned at the distal section of the guidewire shaft to cause the moveable member to move radially outward. An area of the electromagnetic coil proximate to the at least one moveable member may have an opposite magnetic polarity from the magnetic material of the at least one moveable member. The at least one moveable member may be coupled to the guidewire shaft with a hinge. The guidewire assembly may include at least ten moveable members. In addition, the guidewire assembly may include a plurality of rows of moveable members. The electromagnetic coil may be positioned within an interior portion of the guidewire shaft. The at least one moveable member may lie flush with an exterior surface of the guidewire shaft when the guidewire assembly is in the first operating state. The electromagnetic coil may move longitudinally within the guidewire shaft. The at least one movable member may include a north magnetic pole and a south magnetic pole. Also, the electromagnetic coil may include a north magnetic pole and a south magnetic pole. The north magnetic pole of the at least one moveable member may be coupled to the distal section of the guidewire shaft proximate to the south magnetic pole of the electromagnetic coil. The plurality of rows of moveable members may form a helix around the distal portion of the guidewire shaft.

In some aspects, the distal section of the guidewire shaft may include a distal tip, a first shaft extension extending proximally from the distal tip to a section of the guidewire shaft proximal to the distal tip, and a second shaft extension extending proximally from the distal tip to the section of the guidewire shaft proximal to the distal tip. The first shaft extension and the second shaft extension may be interwoven. An exterior surface of the first shaft extension and an exterior surface of the second shaft extension may contact when the guidewire assembly is in the first operating state. Also, the exterior surface of the first shaft extension and the exterior surface of the second shaft extension may not contact and may be radially expanded in the second operating state.

In other aspects of the present disclosure, the guidewire assembly may include one or more of the features below the transitioning from the first operating state to the second operating may include untwisting the first shaft extension from the second shaft extension. Also, the first extension and the second extension may be manufactured with a metal from the nitinol, stainless steel and/or cobalt-chromium families of alloys.

Both the foregoing general description and the following detailed description are exemplary and explanatory only and are not restrictive of the features, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value.

BRIEF DESCRIPTION OF THE FIGURES

The accompanying drawings, which are incorporated in and constitute a part of this specification, illustrate various exemplary embodiments and together with the description, serve to explain the principles of the disclosure.

DETAILED DESCRIPTION

Examples of the present disclosure include systems, devices, and methods to improve the efficacy and safety of minimally-invasive surgeries and other medical procedures. For example, aspects of the present disclosure may relate to medical systems, devices, and methods for delivering a medical device to a portion of a patient's inner anatomy, such as, for example, a procedure to remove kidney stones or other material from a patient's kidney or other organ. In some embodiments, the medical systems of the present disclosure may include a guidewire to deliver a medical tool for diagnosis or treatment of a bodily orifice. The medical devices of the present disclosure include guidewires used to assist in the placement of catheters or other medical devices in body lumens. In particularly, the guidewires of the present disclosure may be configured to have two or more states, a first state similar to current guidewire technology use to track and gain access to target anatomy for a clinical procedure, and a second state where the holding ability of the guidewire is increased to prevent movement of the guidewire from the target anatomy.

Embodiments of the present disclosure are described herein in reference to steerable guide wires for use in minimally invasive medical procedures and/or other medical procedures. For example, it is appreciated that the present invention can be readily adapted for purposes such as, but not limited to, endoscopic retrograde cholangiopancreatography (ERCP), balloon and laser angioplasty, nephrostomy, electrode placement, etc. These applications can all benefit from coupling the body and/or tip of a guidewire to a remote site located internal to the patient's body.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to an operator using the medical device. In contrast, "distal" refers to a position relatively farther away from the operator using the medical device.

Figure 1B:
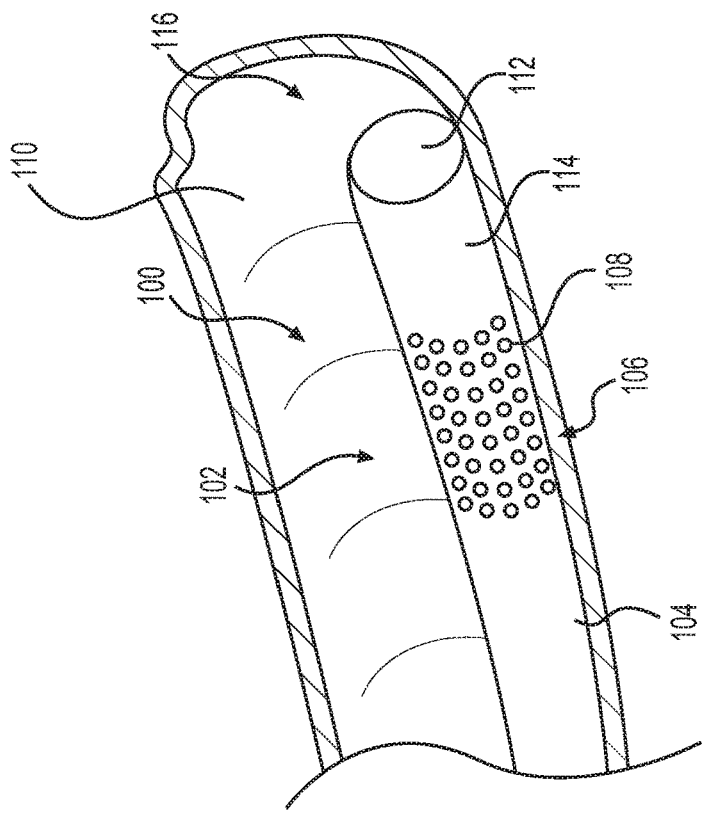
FIG. 1B illustrates the guidewire of FIG. 1A within a lumen shown in cross-section, according to aspects of the present disclosure.
Figure 1A:
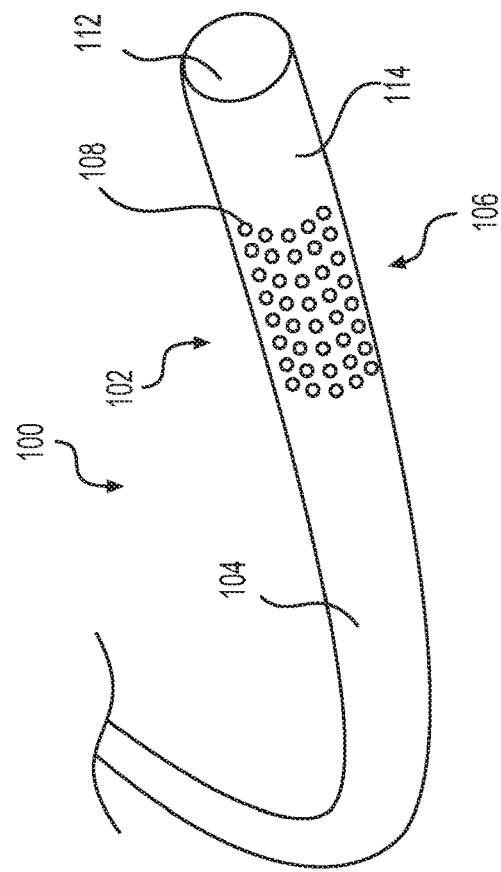
FIG. 1A illustrates an exemplary guidewire, according to aspects of the present disclosure.

FIG. 1A illustrates a distal portion 102 of an exemplary guidewire 100. Guidewire 100 may include a cylindrical body 104 and may extend in a proximal-distal direction. In some examples, cylindrical body 104 may be rectangular, a pentagonal prism, a hexagonal prism, or any other shape extending in a proximal-distal direction with any number of longitudinal sides. The distal portion 102 of guidewire 100 may include one or more holes 108 in one or more outer surfaces of the guidewire. In some examples, holes 108 may be arranged around the circumference of the guidewire 100.

Holes 108 may be arranged in a hole pattern 106, such as the rectangular hole pattern 106 shown in FIGS. 1A and 1B, on an exterior surface 114 of guidewire 100. In other examples, hole pattern 106 may be circular, include multiple clusters of holes, may partially surround the circumference of guidewire 106, and/or may have any other shape. When guidewire 100 is subjected to suction/vacuum force, a hole pattern that only partially surrounds a surface of guidewire 100 will attract only part of an internal body lumen (as shown in FIG. 1B) and resist attracting an entire circumference of an inner body lumen, which could close off the lumen.

In other examples, holes 108 may form a hole pattern 106 on the distal front face 112 of guidewire 100. In some examples, holes 108 may have varying sizes and shapes, with some holes 108 larger than other holes 108. Hole pattern 106 may consist of a single hole 108, such as a single hole 108 about a portion of the circumference of the guidewire. In other examples, hole pattern 106 may consist of 2, 3, 4, 5, 10, 15, 20, 25, 30, 35, 50, 100, 200, or any other number of holes 108. Each of the one or more holes 108 may, in some examples, have a diameter approximately between 0.001" and 0.005", and may be laser drilled holes. Hole pattern 106 may be optimized for a particular procedure and provide traction in some areas and no traction in other areas, for example to avoid sensitive anatomical structures. Holes 108 may be in fluid communication with a lumen positioned within guidewire 100. The lumen may extend in the proximal-distal direction along a longitudinal axis of guidewire 100. In some examples, holes 108 may be connected via the lumen to a vacuum source (not shown) or other auxiliary device or devices, at the proximal end of the guidewire.

Guidewire 100 may be connected at its proximal end to a control unit, a power supply, a display, a vacuum source, and/or any other auxiliary devices known in the art. A control unit may include, for example, any electronic device capable of receiving, storing, processing, generating, and/or transmitting data according to instructions given by one or more programs. Control unit may be operatively coupled to, or part of, one or more of guidewire 100 and the other auxiliary devices, to control one or more aspects of their operation. A power supply may include any suitable power source, and associated connectors (e.g., electrically-conductive wires), for supplying electronic components in the auxiliary devices and guidewire 100 with electrical power. A vacuum source may provide suction or vacuum pressure to one or more holes 108 of guidewire 100, and thereby provide a suction force to couple guidewire 100 to a surface of the interior anatomy of the body and/or assist in holding guidewire 100 proximate to or at target anatomy.

The guide wires according to the present disclosure, such as guidewire 100 or any of the guidewires described herein below, may comprise the same or similar materials and may be fabricated using the same or similar methods known in the art. Guidewire 100 may be controllable via a control unit, handle, or other device known in the art and may have a means for articulating and moving through an interior portion of a body via controls present at a proximal portion of the guidewire or via any auxiliary device. In some examples, guidewire 100 may comprise a metal from the nitinol, stainless steel and/or cobalt-chromium families of alloys, a flexible polytetrafluoroethylene (PTFE) jacket, a heparin coating, a hydrophilic material such as a material similar to a hydrophilic Dream Tip™ made by Boston Scientific, stainless steel, or other materials known in the art. Guidewire 100 may be made of, partially made of, coated by, or otherwise include, gold, platinum, stainless steel with nickel, titanium, tungsten.

In some examples, guidewire 100 may include two operating states that may be controlled by the user via an auxiliary device, a handle present at a proximal portion of the guidewire, or any other actuation mechanism included in the guidewire or connected to the guidewire, wirelessly or by any other means. In some examples, a first operating state of guidewire 100 may be for positioning the guidewire proximate to target anatomy, may require a vacuum source to be in an off position, and may be used or configured for navigating through one or more body lumens inside of a patient. A second operating state of guidewire 100 may be for increasing the holding ability of guidewire 100 by exerting a suction force on one or more surfaces of tissue within a patient. In some examples, the second operating state may be initiated by actuating a vacuum source that is in fluid communication with holes 108, via an internal lumen within the guidewire or otherwise, and may be actuated from an actuator located at or near the proximal portion of guidewire 100 (not shown). In some examples, when guidewire 100 is transitioned from its first operating state to its second operating state, guidewire 100 will couple to an interior wall of a body lumen or other surface within the body of a patient.

FIG. 1B illustrates a perspective view of guidewire 100 positioned within a body lumen 116, shown in cross-section. In FIG. 1B, guidewire 100 is positioned abutting the inner surface 110 of body lumen 116 and is in the second operating state discussed above. As shown in FIG. 1B, the distal portion 102 of guidewire 100 is coupled to an inner surface 110 of body lumen 116, with a portion of hole pattern 106 contacting inner surface 110 of body lumen 116. In some examples, a suction force from holes 108 of hole pattern 106 facilitates coupling the distal portion 102 of guidewire 100 to inner surface 110 of body lumen 116. When guidewire 100 is in the second operating state, the suction force may be provided by a vacuum source located at the proximal end of guidewire 100 and may prevent guidewire 100 from moving from a region proximate to target anatomy. In some examples, when guidewire 100 transitions from a second operating state to a first operating state, such as by turning off a vacuum source connected to holes 108, guidewire 100 may release from inner surface 110 of body lumen 116. An actuation mechanism may transition guidewire 100 from its first operating state to its second operating state, or vice versa, and may be operated by the user or an assistant to the user, such a physician or nurse. Guidewire 100 may provide a user with an actuatable anchoring mechanism to apply a suction force within a body of a patient in order to couple the distal portion 102 of guidewire 100 to interior anatomy and hold the distal portion 102 proximate to target anatomy while conducting a procedure.

Figure 2B:
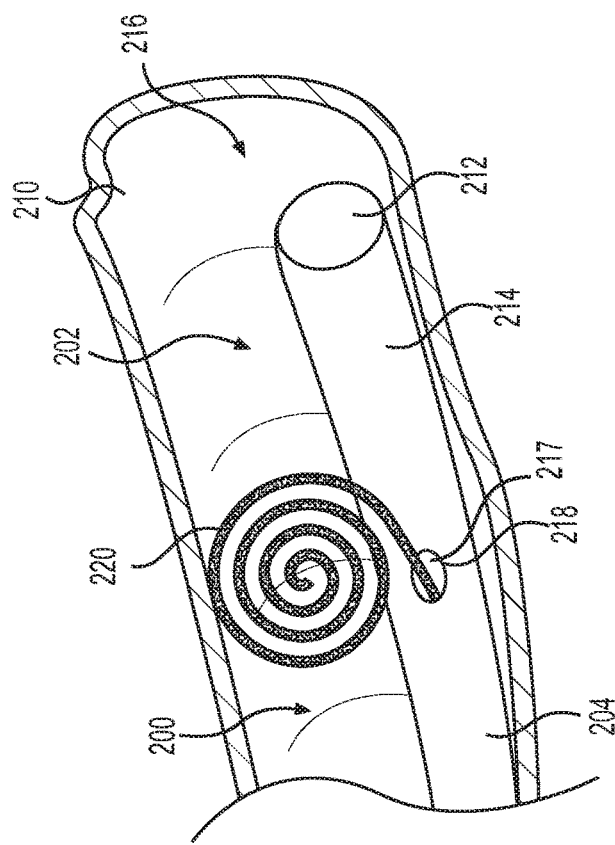
FIG. 2B illustrates the guidewire of FIG. 2A within a lumen shown in cross-section, according to aspects of the present disclosure.
Figure 2A:
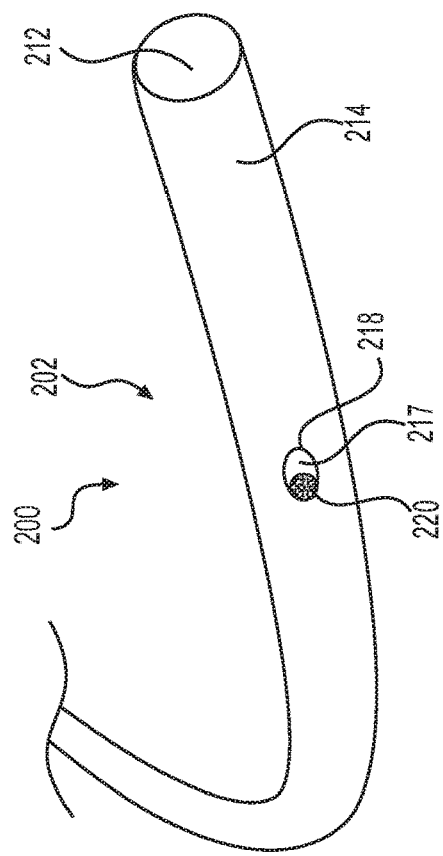
FIG. 2A illustrates an exemplary guidewire, according to aspects of the present disclosure.

FIG. 2A shows another exemplary embodiment of a guidewire 200, which may have any of the previously described features in relation to guidewire 100. Guidewire 200 may include a distal portion 202, cylindrical body 204, exterior surface 214, and distal front face 212. In some examples, guidewire 200 may include a lumen 217 positioned within guidewire 200 and extending in the proximal-distal direction. Lumen 217 may include a proximal opening (not shown) and a distal opening 218. Distal opening 218 may be positioned anywhere on exterior surface 214 or distal front face 212. Guidewire 200 may include a wire 220 positioned within lumen 217. In some examples, wire 220 may be configured to move in a proximal-distal direction within lumen 217 and may be pushed out of opening 218 when a user is operating guidewire 200. For example, a user may push a proximal portion of wire 220 from the proximal end of guidewire 200 to extend a distal portion of wire 220 outward from distal opening 218.

FIG. 2B illustrates a perspective view of guidewire 200 positioned within a body lumen 216, shown in cross-section. As shown in FIG. 2B, wire 220 may be pushed outward from distal opening 218 and may form a spiral shape when extended outward from distal opening 218. Wire 220 may comprise a pre-shaped material, such as a pre-shaped metal from the nitinol, stainless steel and/or cobalt-chromium families of alloys, and may assume its pre-set shape upon exiting opening 218. For example, wire 220 may have a pre-set shape that the wire may assume, without the aid of a user, when outside of lumen 217. Although wire 220 is shown with a pre-shaped spiral structure in FIG. 2B, inner wire 220 may have any pre-shaped structure, such as an S-curved shape or helical spiral. When pushed outward from opening 218, inner wire 220 may assume its pre-set shape, radially expanding the distal portion of guidewire 200 so that guidewire 200 presses against inner surface 210 of body lumen 216 and thereby inhibits movement of guidewire 200 within body lumen 216. In some examples, wire 220 may contact inner surface 210 of body lumen 216 and apply a radial force on inner surface 210 of body lumen 216 to prevent movement of guidewire 200 within body lumen 216. As the user pushes inner wire 220 in the proximal-distal direction, a distal portion of inner wire 220 may extend outward from opening 218 to increase the size of the portion of wire 220 outside of lumen 217 and exposed to a patient's anatomy, such as body lumen 216. The ability to have the inner wire 220 expand outward from the exterior surface 214 of guidewire 200 may enable the user to control the size of the size of the deployed inner wire 220 outside lumen 217 and make adjustments in the position of guidewire 200 by pushing or pulling on a proximal portion of inner wire 220. The distal portion of wire 220 may be configured to assume a preset configuration when extended outward from opening 218 to engage the body of a patient and inhibit movement of the guidewire 200 in a second operating state of the guidewire 200. In some examples, opening 218 may be positioned on the distal end of guidewire 200, and the distal portion of wire 220 may be configured to assume a preset configuration when extended outward from the distal front face 212 of guidewire 200.

Figure 3B:
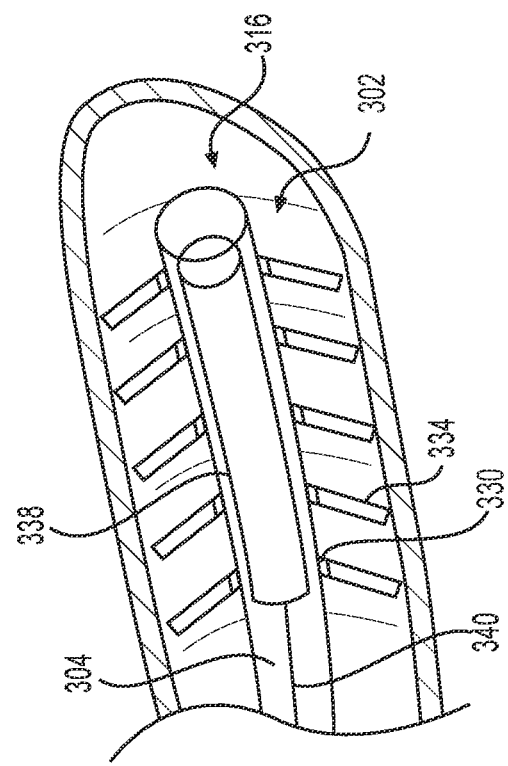
FIG. 3B illustrates the guidewire shown in FIG. 3A within a lumen shown in cross-section, according to aspects of the present disclosure.
Figure 3A:
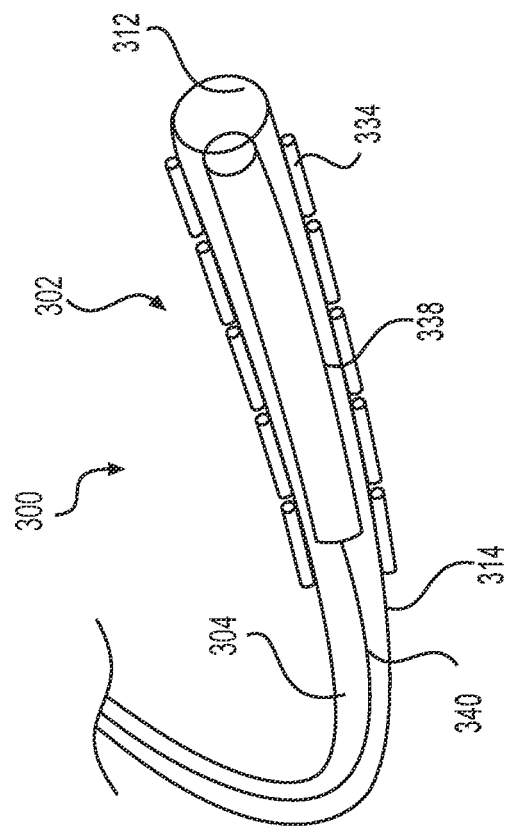
FIG. 3A illustrates an exemplary guidewire, according to aspects of the present disclosure.

FIG. 3A shows yet another exemplary embodiment of a guidewire 300, which may have any of the previously described features in relation to guidewires 100, 200. In some examples, guidewire 300 may include a distal portion 302, cylindrical body 304, a distal front face 312, and an exterior surface 314. An electromagnetic coil 338 may be positioned at a distal portion 302 of guidewire 300 and, in some examples, may be connected to a wire 340 that extends within body 304 to a proximal end of guidewire 300. An electrical power source (not shown) may be connected to electromagnetic coil 338 via wire 340. Such an electrical power source may be located at a proximal portion of guidewire 300 and/or outside of guidewire 300. Electromagnetic coil 338 may be any shape or size, such as cylindrical (shown in FIGS. 3A and 3B), rectangular, toroidal, etc. Electromagnetic coil 338 may be positioned within guidewire 300, on an exterior surface 314 of guidewire 300, and/or protruding from an exterior surface 314 of guidewire 300. Electromagnetic coil 338 may produce a magnetic field when electrical energy is sent from a power source to electromagnetic coil 338.

Guidewire 300 may further include one or more protrusions 334 coupled to an exterior surface 314 of its distal portion 302. In other examples, protrusions 334 may be partially or fully receded within the surface 314 of guidewire 300. In such embodiments, protrusions 334 may lie flush with surface 314 in a first configuration. In some examples, one or more protrusions 334 may be coupled to a proximal portion of guidewire 300, between the proximal and distal ends of guidewire 300, or any other location along the exterior surface of guidewire 300.

Protrusions 334 may comprise a permanent or temporary magnet material, including a core and/or coating of such material. The magnet material may provide a means for protrusions 334 to interact with electromagnetic coil 338. In some examples, the magnet material may be, or may be a combination of two or more of, Neodymuium (NdFeB), Samarium-Cobalt (SmCo), Ferrite, or Alnico (AlNiCo). Protrusions 334 may be any shape or size, such as cylindrical protrusions shown in FIGS. 3A and 3B. In some examples, protrusions may be rectangular or circular in cross-section, contoured to the exterior surface 314 of guidewire 300, or irregularly shaped. In some examples, protrusions 334 may be approximately between 0.015 and 0.040 inches in length, between 0.018-0.035 inches in length, or between 0.025-0.035 inches in length. In some examples, protrusions 334 may be bendable and/or may include hinges 330 (shown in FIG. 3B). For example, each protrusion 334 may be separately coupled to guidewire 300 with a hinge 330, such as a living hinge. In other examples, a single hinge 330 may couple multiple different protrusions 334 to guidewire 300. In some examples, protrusions 334 may be directly coupled to an exterior surface 314 of guidewire 300, such as directly glued or fastened to an exterior surface 314. In other examples, protrusions 334 may be formed integrally with surface 314. Protrusions 334 may have an irregular or roughened surface configured to grip tissue, an adhesive surface to adhere to tissue, and/or rounded, atraumatic tips opposite where the protrusions 334 are fastened to guidewire 300.

In some examples, protrusions 334 may be positioned on exterior surface 314 of guidewire 300 in a single row along the longitudinal axis of guidewire 300, and may be positioned such that each protrusion 334 is coupled to guidewire 300 by a hinge 330 at a distalmost portion of each protrusion 334. In other examples, protrusions 334 may be positioned in two rows diametrically opposite along the longitudinal axis of guidewire 300 as shown in FIGS. 3A and 3B. In some examples, guidewire 300 may include more than two rows of protrusions 334 spaced about the circumference of guidewire 300. Alternatively, guidewire 300 may include a helical arrangement of protrusions 334 about guidewire 300, such as about its exterior surface 314, or any other desired arrangement.

An electrical power source may be actuated by a user of guidewire 300 to allow electrical current to flow through wire 340 and to electromagnetic coil 338. When electrical current flows to electromagnetic coil 338, a magnetic force may be exerted on protrusions 334 causing protrusions 334 to extend outward away from the exterior surface 314 of guidewire 300. By extending outward from guidewire 300, protrusions 334 may increase friction between guidewire 300 and tissue of the patient, and assist the user in maintaining the position of guidewire 300 within the body of the patient. In some examples, hinges 330 may prevent protrusions 334 from extending beyond a specific angle relative to the exterior surface 314 of guidewire 300, and may be configured to allow protrusions 334 to extend outward from guidewire 300 at a 30 degree angle, a 45 degree angle, a 60 degree angle, a 90 degree angle, or any other angle when electromagnetic coil 338 is turned on. In some embodiments, the angle can vary depending on the amount of magnetic force applied by the power source, so that guidewire 300 may be suitable for varying sizes of body lumens. When a user stops the flow of electricity to electromagnetic coil 338, such as by actuating a button at a proximal portion of guidewire 300, protrusions may move towards the exterior surface 314 of guidewire 300. Similar to guidewire 100, guidewire 300 may have two operating states that may be controlled by the user via an auxiliary device, handle present at a proximal portion of the guidewire, or any other actuation mechanism included in the guidewire or connected to the guidewire, wirelessly or by any other means. In some examples, a first operating state of guidewire 300 may be when no electrical current flows to electromagnetic coil 338 and guidewire 300 is configured to move within the body of a patient. A second operating state of guidewire 300 may be when electrical current flows to electromagnetic coil 338 and, as a result, protrusions 334 are extended outward from the exterior surface 314 of guidewire 300 (shown in FIG. 3B). When in a second operating state, guidewire 300 may resist movement with the body of a patient because of increased friction with bodily tissue.

The opposite polarity of the magnetic portion of each protrusion 334 and the electromagnetic coil 338 may exert a magnetic force to radially extend protrusions 334 outward from exterior surface 314. Electromagnetic coil 338 and one or more protrusions 334 may each include a north magnetic pole and a south magnetic pole. In some examples, electromagnetic coil 338 may include a south magnetic pole at a distal portion of the electromagnetic coil 338 and a north magnetic pole at a proximal portion of the electromagnetic coil 338. In other examples, electromagnetic coil 338 may include a north magnetic pole at a distal portion of the electromagnetic coil 338 and may include a south magnetic pole at a proximal portion of the electromagnetic coil 338. In some examples, one or more protrusions 334 positioned proximate to the south magnetic pole of the electromagnetic coil 338 may include a north magnetic pole proximate to the portion of protrusion 334 that is coupled to guidewire 300, such as proximate to hinge 330 coupling protrusion 334 to guidewire 300, and include a south magnetic pole at a free end of protrusion 334. Similarly, one or more protrusions 334 positioned proximate to the north magnetic pole of the electromagnetic coil 338 may include a south magnetic pole proximate to the portion of protrusion 334 that is coupled to guidewire 300, such as proximate to hinge 330 coupling protrusion 334 to guidewire 300, and include a north magnetic pole at the free end of protrusion 334. In some examples, the polarity of the electromagnetic coil may be reversed in order to attract protrusion 334 to the surface of the guidewire 300 to hold a longitudinal surface of protrusion 334 flush with the exterior surface of guidewire 300 when advancing or withdrawing the guidewire 300.

FIG. 3B illustrates a perspective view of guidewire 300 positioned within a body lumen 316, shown in cross-section. When protrusions 334 are in the extended position (shown in FIG. 3B), barbs may be created at the distal portion 302 of guidewire 300. Depending on the needs of a procedure, various configurations of protrusions 334 may be used, such as multiple small protrusions along the surface of guidewire 300 or one or two larger protrusions. By utilizing an electromagnet, the user may switch between first and second operating states of guidewire 300 to facilitate movement within the body of a patient or holding a position proximal to target anatomy.

In some examples, electromagnetic coil 338 may be moveable. For example, electromagnetic coil 338 may be moveable in a proximal-distal direction in a lumen within guidewire 300. In some examples, the user may move electromagnetic coil 338 longitudinally while applying electrical energy to electromagnetic coil 338, which may cause only certain protrusions 334 to move outwardly from guidewire 300. For example, as the electrically charged electromagnetic coil 338 moves longitudinally, the protrusions 334 that have a magnetic pole proximate or close to an opposite magnetic pole of the electromagnetic coil 338 will move outwardly from guidewire 300. When electromagnetic coil 338 is configured to move, the user may selectively deploy protrusions 334 while not deploying other protrusions 334.

Figure 4B:
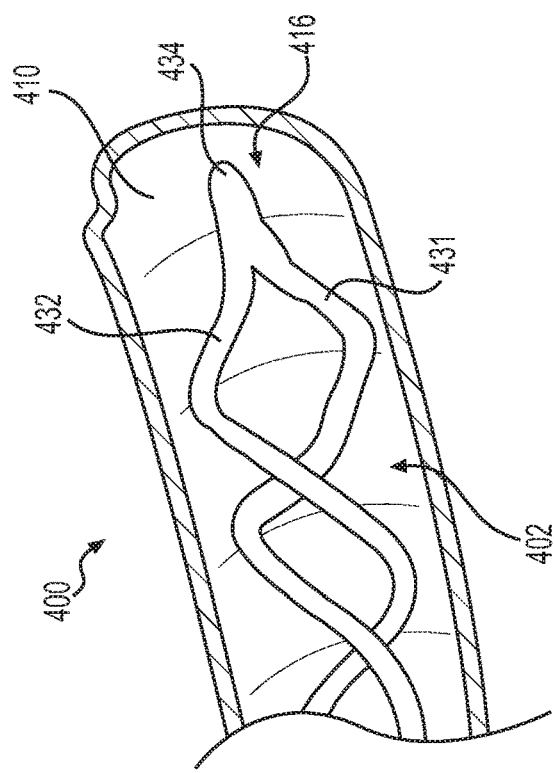
FIG. 4B illustrates the guidewire shown in FIG. 4A within a lumen shown in cross-section, according to aspects of the present disclosure.
Figure 4A:
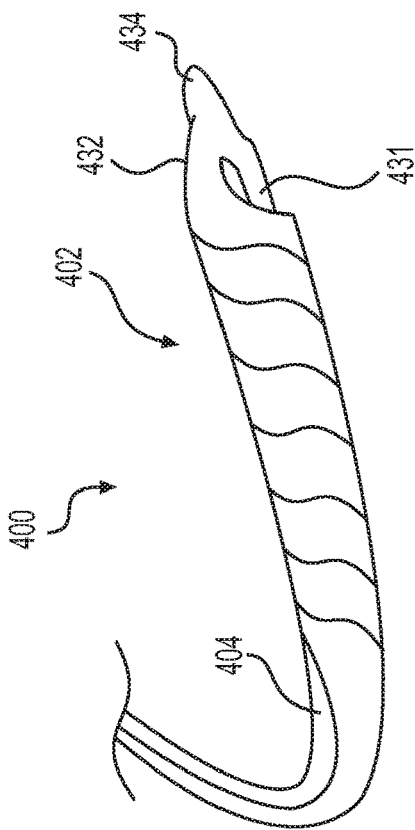
FIG. 4A illustrates an exemplary guidewire, according to aspects of the present disclosure.

FIG. 4A shows another exemplary embodiment of a guidewire 400, which may have any of the previously described features in relation to guidewires 100, 200, 300. In some examples, guidewire 400 may include a distal portion 402, a cylindrical body 404, and a distal tip 434. Distal portion 402 of guidewire 400 may comprise a helical structure with two portions 431, 432 extending proximally from distal tip 434. Portions 431, 432 of guidewire 400 may extend the entire length of guidewire 400, or may terminate at a section of guidewire 400 proximal to distal tip 434. In some examples, portions 431, 432 may form interwoven helices. Guidewire 400 or portions of guidewire 400 may comprise a metal from the nitinol, stainless steel and/or cobalt-chromium families of alloys. Proximal ends of portions 431, 432 may be coupled to an actuation means (e.g. a handle or other actuator) that may rotate one or both of the portions 431, 432 to radially expand distal portion 402 of guidewire 400. For example, portion 431 and 432 may be rotated relatively to each other to untwist themselves at distal portion 402, allowing portion 431, 432 to expand outwardly. Each of portions 431, 432 may be cylindrical and may be shaped so that, when in the configuration of FIG. 4A, they mesh together for guidewire 400 to have a smooth outer surface. This will permit better tracking through a body lumen.

FIG. 4B illustrates a perspective view of guidewire 400 positioned within a body lumen 416, shown in cross-section. Similar to guidewires 200, 300, guidewire 400 may have two operating states. In some examples, guidewire 400 may have a first operating state which may be when portions 431, 432 are twisted together, contacting each other, and aligned to form a low profile, cylindrical shape, as shown in FIG. 4A. In such a first operating state, guidewire 400 may be configured to move within the body of a patient. In some examples, a second operating state of guidewire 400 may be when portions 431, 432 are untwisted and/or a force is applied to portions 431, 432 to cause radial expansion of guidewire 400, as shown in FIG. 4B. When in such a second operating state, portions 431, 432 may have larger helical diameters compared to a first operating state, and the radial diameter of guidewire 400 may increase relative to a first operating state. As shown in FIG. 4B, the radial expansion of portions 431, 432 may increase contact with an inner surface 410 of a body lumen 416 within a patient. In some examples, the user may change from a first operating state of guidewire 400 to a second operating state with an actuator present at a proximal portion of guidewire 400 and/or with an auxiliary device. In some examples, guidewire 400 may be used to dilate a body lumen 416 of a patient during a procedure. In some examples, portions 431, 432 may be interwoven and an exterior surface of portion 431 and an exterior surface of portion 432 may contact when guidewire 400 is in a first operating state. In some examples, the exterior surface of portion 431 and the exterior surface of portion 432 may not be contacting and may be radially expanded in a second operating state.

During use, any one of guidewires 100, 200, 300, 400 may be introduced into a body cavity or incision of a patient. The user may then insert the guidewire into a body lumen and navigate using auxiliary controls to move a distal portion of the guidewire. The user may manipulate the guidewire, such as guidewire 100, such that its distal portion 102 is proximate to target anatomy, such as a kidney stone, for example. Once the user has positioned the guidewire proximate to a target anatomy, the user may actuate a transition means, such as turning on a vacuum source to apply suction force to holes 108 of guidewire 100, and transition the guidewire from a first operating state to a second operating state. The guidewire may then couple itself to, and/or increase friction against, one or more surfaces of the patient's anatomy and may allow the user to guide other medical devices using the guidewire. The increased friction and/or coupling to the surface of patient's anatomy may allow a user to continually maintain the guidewire's position at the target anatomy, even while moving other medical devices along the guidewire and/or proximate to the guidewire. For example, the user may insert a guidewire into a patient's body and move the guidewire to target anatomy within the patient's body, actuate an actuator to transition the guidewire from a first operating state to a second operating state. The guidewire may then, in some examples, couple itself to a surface within the body via vacuum suction, and then the user may insert additional medical devices adjacent to target anatomy and the guidewire while guidewire maintains its position within the body, such as inserting medical devices with the aid of the guidewire to reach target anatomy. After completion of the medical procedure, or when the user would like to change the positioning of the guidewire from one target anatomy region to a different target anatomy region, the user may actuate an auxiliary device to transition the guidewire from a second operating state to a first operating state configured to allow guidewire to move through the patient's anatomy and minimize friction between the guidewire and surfaces of patient's anatomy.

The disclosed guidewires 100, 200, 300, 400 and portions thereof shown in the figures and discussed above facilitate positioning of other medical devices during a medical procedure. The guidewires 100, 200, 300, 400 and portions thereof may help enable efficient and effective procedures by maintaining guidewire positioning at target anatomy regions, while also providing a consistent guide for positioning other medical devices proximate to a target anatomy region.

It is contemplated that the guidewires, systems and methods discussed herein may be applicable to any endoscopic and/or minimally invasive procedure. For example, the systems, devices, and methods discussed above may be used during a percutaneous nephrolithotomy/nephrolithotripsy (PCNL). The systems, devices, and methods discussed above may also be used in procedures to remove ureteral stones, gallstones, bile duct stones, polyps, stent placement, gastroenteral anastomosis, choledochoduodenostomy, etc.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A guidewire assembly for positioning within a body of a patient comprising:
   a guidewire shaft having a proximal section and a distal section, wherein the distal section is configured to move within the body of a patient when the guidewire assembly is in a first operating state, and wherein the distal section is configured to expand radially outward when the guidewire assembly is in a second operating state to engage an interior surface of the body and inhibit movement of the guidewire shaft;
   at least one movable member coupled to the distal section of the guidewire shaft, wherein the moveable member comprises a magnetic material and moves radially outward when the guidewire assembly transitions from the first operating state to the second operating state; and
   an electromagnetic coil positioned at the distal section of the guidewire shaft, to cause the moveable member to move radially outward when the guidewire assembly is in the second operating state;
   wherein: the at least one movable member includes a north magnetic pole and a south magnetic pole; the electromagnetic coil includes a north magnetic pole and a south magnetic pole; and the north magnetic pole of the at least one moveable member is coupled to the distal section of the guidewire shaft proximate to the south magnetic pole of the electromagnetic coil.

2. The guidewire assembly of claim 1, wherein an area of the electromagnetic coil proximate to the at least one moveable member has an opposite magnetic polarity from the magnetic material of the at least one moveable member.

3. The guidewire assembly of claim 1, wherein the at least one moveable member is coupled to the guidewire shaft with a hinge.

4. The guidewire assembly of claim 1, further comprising at least ten moveable members.

5. The guidewire assembly of claim 4, further comprising a plurality of rows of moveable members.

6. The guidewire assembly of claim 5, wherein the plurality of rows of moveable members form a helix around the distal portion of the guidewire shaft.

7. The guidewire assembly of claim 1, wherein the at least one moveable member lies flush with an exterior surface of the guidewire shaft when the guidewire assembly is in the first operating state.

8. The guidewire assembly of claim 1, wherein the electromagnetic coil moves longitudinally within the guidewire shaft.

9. The guidewire assembly of claim 1, wherein the distal section of the guidewire shaft comprises:
   a distal tip;
   a first shaft extension extending proximally from the distal tip to a section of the guidewire shaft proximal to the distal tip; and
   a second shaft extension extending proximally from the distal tip to the section of the guidewire shaft proximal to the distal tip;
   wherein:
   the first shaft extension and the second shaft extension are interwoven;

an exterior surface of the first shaft extension and an exterior surface of the second shaft extension contact when the guidewire assembly is in the first operating state; and the exterior surface of the first shaft extension and the exterior surface of the second shaft extension are not contacting and are radially expanded in the second operating state.

10. The guidewire assembly of claim 9, wherein the transitioning from the first operating state to the second operating includes untwisting the first shaft extension from the second shaft extension.

11. The guidewire assembly of claim 9, wherein the first extension and the second extension include a metal from the nitinol, stainless steel and/or cobalt-chromium families of alloys.

12. The guidewire assembly of claim 1, wherein the electromagnetic coil is positioned within an interior portion of the guidewire shaft.

13. A guidewire assembly for positioning within a body of a patient comprising:
 a guidewire shaft having a proximal section and a distal section, wherein the distal section is configured to move within the body of a patient when the guidewire assembly is in a first operating state, and wherein the distal section is configured to expand radially outward when the guidewire assembly is in a second operating state to engage an interior surface of the body and inhibit movement of the guidewire shaft;
 at least one movable member coupled to the distal section of the guidewire shaft, wherein the moveable member comprises a magnetic material and moves radially outward when the guidewire assembly transitions from the first operating state to the second operating state; and
 an electromagnetic coil positioned at the distal section of the guidewire shaft, to cause the moveable member to move radially outward when the guidewire assembly is in the second operating state;
 the at least one movable member includes a north magnetic pole and a south magnetic pole;
 the electromagnetic coil includes a north magnetic pole and a south magnetic pole; and
 the south magnetic pole of the at least one moveable member is coupled to the distal section of the guidewire shaft proximate to the north magnetic pole of the electromagnetic coil.

14. The guidewire assembly of claim 13, wherein an area of the electromagnetic coil proximate to the at least one moveable member has an opposite magnetic polarity from the magnetic material of the at least one moveable member.

15. The guidewire assembly of claim 13, wherein the at least one moveable member is coupled to the guidewire shaft with a hinge.

16. The guidewire assembly of claim 13, further comprising at least ten moveable members.

17. The guidewire assembly of claim 13, further comprising a plurality of rows of moveable members.

18. The guidewire assembly of claim 17, wherein the plurality of rows of moveable members form a helix around the distal portion of the guidewire shaft.

19. The guidewire assembly of claim 13, wherein the at least one moveable member lies flush with an exterior surface of the guidewire shaft when the guidewire assembly is in the first operating state.

20. The guidewire assembly of claim 13, wherein the electromagnetic coil moves longitudinally within the guidewire shaft.

* * * * *